United States Patent
Babaev (10) Patent No.: US 6,478,754 B1
(45) Date of Patent: Nov. 12, 2002

(54) ULTRASONIC METHOD AND DEVICE FOR WOUND TREATMENT

(75) Inventor: Eilaz Babaev, Minnetonka, MN (US)

(73) Assignee: Advanced Medical Applications, Inc., Eden Prairie, MN (US)

( * ) Notice: Subject to any disclaimer, the term of this patent is extended or adjusted under 35 U.S.C. 154(b) by 25 days.

(21) Appl. No.: 09/840,416

(22) Filed: Apr. 23, 2001

(51) Int. Cl.[7] ................................................. A61H 1/00

(52) U.S. Cl. ................................. 601/2; 601/3; 604/22; 604/24

(58) Field of Search ................................. 600/437, 439; 601/2, 3; 604/22, 24, 68–73, 890.1; 606/1

(56) References Cited

U.S. PATENT DOCUMENTS

| | | |
|---|---|---|
| 3,275,059 A | 9/1966 | McCullough |
| 3,392,916 A | 7/1968 | Engstrom et al. |
| 3,561,444 A | 2/1971 | Boucher |
| 3,860,173 A | 1/1975 | Sata |
| 4,052,004 A | 10/1977 | Martin et al. |
| 4,085,893 A | 4/1978 | Durley, III |
| 4,153,201 A | 5/1979 | Berger et al. |
| 4,251,031 A | 2/1981 | Martin et al. |
| 4,271,705 A | 6/1981 | Crostack |
| 4,294,407 A | 10/1981 | Reichl et al. |
| 4,301,093 A | 11/1981 | Eck |
| 4,301,968 A | 11/1981 | Berger et al. |
| 4,309,989 A | 1/1982 | Fahim |
| 4,319,155 A | 3/1982 | Nakai et al. |
| 4,334,531 A | 6/1982 | Reichl et al. |
| 4,352,459 A | 10/1982 | Berger et al. |
| 4,428,531 A | 1/1984 | Martin |
| 4,466,571 A | 8/1984 | Muhlbauer |
| 4,530,360 A | 7/1985 | Duarte |
| 4,541,564 A | 9/1985 | Berger et al. |
| 4,582,654 A | 4/1986 | Karnicky et al. |
| 4,619,400 A | 10/1986 | Van Der Burgt |
| 4,642,581 A | 2/1987 | Erickson |
| 4,655,393 A | 4/1987 | Berger |
| 4,659,014 A | 4/1987 | Soth et al. |
| 4,679,551 A | 7/1987 | Anthony |

(List continued on next page.)

FOREIGN PATENT DOCUMENTS

| | | |
|---|---|---|
| EP | 0 156 4009 A2 | 2/1985 |
| EP | 0 437 155 B1 | 2/1990 |
| EP | 0 657 226 B1 | 11/1994 |
| GB | 2 099 710 A | 12/1982 |
| GB | 2 101 500 A | 1/1983 |
| JP | 2000237275 A2 | 9/2000 |
| WO | WO 96/35383 | 11/1996 |

OTHER PUBLICATIONS

Journal of Burn Care & Rehabilitation; vol. 21, No. 4; Jul./Aug. 2000 pp. 333–338.

Design and Application of Low–Frequency Ultrasound and Its Combination With Laser Radiation in Surgery and Therapy—Critical Reviews in Biomedical Engineering; 2001; pp. 502–519.

*Primary Examiner*—Marvin M. Lateef
*Assistant Examiner*—Runa Shah Qaderi
(74) *Attorney, Agent, or Firm*—Carter, Deluca, Farrell & Schmidt, LLP (57) ABSTRACT

The method and device of the present invention for ultrasound wound treatment includes a transducer to produce ultrasonic waves. The ultrasonic transducer has tip with the distal end (radiation surface). A liquid is directed to the radiation surface through central orifice or separate tube wherein an directed atomized particle spray of the liquid is created upon contact of the liquid with the radiation surface. The spray directed to the wound from at least 0.1 inches transmits ultrasound waves trough particles and has an irrigation, mechanical cleansing, liquid energizing and bactericide effect.

22 Claims, 4 Drawing Sheets

U.S. PATENT DOCUMENTS

| | | |
|---|---|---|
| 4,726,523 A | 2/1988 | Kokubo et al. |
| 4,726,525 A | 2/1988 | Yonekawa et al. |
| 4,733,820 A | 3/1988 | Endo et al. |
| 4,756,478 A | 7/1988 | Endo et al. |
| 4,783,003 A | 11/1988 | Hirabayashi et al. |
| 4,790,479 A | 12/1988 | Matsumoto et al. |
| 4,793,339 A | 12/1988 | Matsumoto et al. |
| 4,850,534 A | 7/1989 | Takahashi et al. |
| 4,877,989 A | 10/1989 | Drews et al. |
| 4,905,671 A | 3/1990 | Senge et al. |
| 4,930,700 A | 6/1990 | McKown |
| 4,941,618 A | 7/1990 | Hildebrand et al. |
| 4,961,885 A | 10/1990 | Avrahami et al. |
| 5,002,059 A | 3/1991 | Crowley et al. |
| 5,040,537 A | 8/1991 | Katakura |
| 5,063,922 A | 11/1991 | Hakkinen |
| 5,076,266 A | 12/1991 | Babeav |
| 5,104,042 A | 4/1992 | McKown |
| 5,115,805 A | 5/1992 | Bommannan et al. |
| 5,134,993 A | 8/1992 | van der Linden et al. |
| 5,163,433 A | 11/1992 | Kagawa et al. |
| 5,172,692 A | 12/1992 | Kulow et al. |
| 5,186,162 A | 2/1993 | Talish et al. |
| 5,197,946 A | 3/1993 | Tachibana |
| 5,211,160 A | 5/1993 | Talish et al. |
| 5,231,975 A | 8/1993 | Bommannan et al. |
| 5,269,291 A | 12/1993 | Carter |
| 5,315,998 A  * | 5/1994 | Tachibana et al. ........ 424/94.63 |
| 5,316,000 A | 5/1994 | Chapelon et al. |
| 5,318,014 A | 6/1994 | Carter |
| 5,323,769 A | 6/1994 | Bommannan et al. |
| 5,324,255 A | 6/1994 | Passafaro et al. |
| 5,345,940 A | 9/1994 | Seward et al. |
| 5,347,998 A | 9/1994 | Hodson et al. |
| 5,362,309 A | 11/1994 | Carter |
| 5,374,266 A | 12/1994 | Kataoka et al. |
| 5,380,411 A | 1/1995 | Schlief |
| 5,393,296 A | 2/1995 | Rattner |
| 5,437,606 A | 8/1995 | Tsukamoto |
| 5,515,841 A | 5/1996 | Robertson et al. |
| 5,515,842 A | 5/1996 | Ramseyer et al. |
| 5,516,043 A | 5/1996 | Manna et al. |
| 5,520,166 A | 5/1996 | Ritson et al. |
| 5,520,612 A | 5/1996 | Winder et al. |
| 5,527,350 A | 6/1996 | Grove et al. |
| 5,529,572 A | 6/1996 | Spector |
| 5,545,124 A | 8/1996 | Krause et al. |
| 5,551,416 A  * | 9/1996 | Stimpson et al. ...... 128/200.14 |
| 5,554,172 A | 9/1996 | Horner et al. |
| 5,556,372 A | 9/1996 | Talish et al. |
| 5,573,497 A | 11/1996 | Chapelon |
| 5,616,140 A | 4/1997 | Prescott |
| 5,626,554 A | 5/1997 | Ryaby et al. |
| 5,643,179 A | 7/1997 | Fujimoto |
| 5,656,016 A | 8/1997 | Ogden |
| 5,658,323 A | 8/1997 | Miller |
| 5,699,805 A | 12/1997 | Seward et al. |
| 5,707,402 A | 1/1998 | Heim |
| 5,707,403 A | 1/1998 | Grove et al. |
| 5,730,705 A | 3/1998 | Talish et al. |
| 5,735,811 A | 4/1998 | Brisken |
| 5,743,863 A | 4/1998 | Chapelon |
| 5,752,924 A | 5/1998 | Kaufman et al. |
| 5,762,616 A | 6/1998 | Talish |
| 5,785,972 A  * | 7/1998 | Tyler .......................... 424/539 |
| 5,835,678 A | 11/1998 | Li et al. |
| 5,843,139 A | 12/1998 | Goedeke et al. |
| 5,879,314 A | 3/1999 | Peterson et al. |
| 5,879,364 A | 3/1999 | Bromfield et al. |
| 5,882,302 A | 3/1999 | Driscoll, Jr. et al. |
| 5,894,841 A | 4/1999 | Voges |
| 5,947,921 A | 9/1999 | Johnson et al. |
| 5,960,792 A | 10/1999 | Lloyd et al. |
| 5,989,245 A | 11/1999 | Prescott |
| 6,001,069 A | 12/1999 | Tachibana et al. |
| 6,014,970 A | 1/2000 | Irvi et al. |
| 6,024,718 A | 2/2000 | Chen et al. |
| 6,026,808 A | 2/2000 | Armer et al. |
| 6,027,495 A | 2/2000 | Miller |
| 6,041,253 A | 3/2000 | Kost et al. |
| 6,061,597 A | 5/2000 | Rieman et al. |
| 6,076,519 A | 6/2000 | Johnson |
| 6,083,159 A | 7/2000 | Driscoll, Jr. et al. |
| 6,095,141 A | 8/2000 | Armer et al. |
| 6,098,620 A | 8/2000 | Lloyd et al. |
| 6,102,298 A | 8/2000 | Bush et al. |
| 6,106,547 A | 8/2000 | Huei-Jung |
| 6,113,558 A | 9/2000 | Rosenschein et al. |
| 6,113,570 A | 9/2000 | Siegel et al. |
| RE36,939 E  * | 10/2000 | Tachibana et al. ............ 604/22 |
| 6,158,431 A | 12/2000 | Poole |
| 6,176,839 B1 | 1/2001 | DeLuis et al. |
| 6,186,963 B1 | 2/2001 | Schwarze et al. |
| 6,190,315 B1 | 2/2001 | Kost et al. |
| 6,190,336 B1 | 2/2001 | Duarte et al. |
| 6,206,842 B1 | 3/2001 | Tu et al. |
| 6,206,843 B1 | 3/2001 | Iger et al. |
| 6,231,528 B1 | 5/2001 | Kaufman et al. |
| 6,234,990 B1 | 5/2001 | Rowe et al. |
| 6,251,099 B1 * | 6/2001 | Kollias et al. ................ 604/20 |
| 6,273,864 B1 | 8/2001 | Duarte et al. |
| 6,321,109 B2 | 11/2001 | Ben-Haim et al. |
| 6,322,527 B1 | 11/2001 | Talish |
| 6,325,769 B1 | 12/2001 | Klopotek |

* cited by examiner

ULTRASONIC METHOD AND DEVICE FOR WOUND TREATMENT

FIELD OF THE INVENTION

The present invention relates to a method of using ultrasonic waves in wound treatment. In particular, the present invention relates to a method of spraying a wound surface using ultrasonic waves for delivering drugs, killing bacteria, cleansing a surface, increasing blood flow and stimulating healthy tissue cells.

BACKGROUND OF THE INVENTION

Ultrasonic waves have been widely used in medical applications, including both diagnostics and therapy, as well as in many industrial applications. One diagnostic use of ultrasound waves includes using ultrasonic waves to detect underlying structures in an object or human tissue. In this method, an ultrasonic transducer is placed in contact with the tissue (or object) via a coupling medium, and high frequency (1–10 MHz) ultrasonic waves are directed into the tissue. Upon contact with underlying structures, the waves are reflected back to a receiver adjacent the transducer. By comparison of the signals of an ultrasonic wave as sent with the reflected ultrasonic wave as received, an image of the underlying structure can be produced. This technique is particularly useful for identifying boundaries between components of tissue and can be used to detect irregular masses, tumors, and the like.

Two therapeutic medical uses of ultrasonic waves include aerosol mist production and contact physiotherapy. Aerosol mist production makes use of a nebulizer or inhaler to produce an aerosol mist for creating a humid environment and delivering drug to the lung.

Ultrasonic nebulizers operate by passing ultrasonic waves of sufficient intensity through a liquid, the waves being directed at an air-liquid interface of the liquid from a point underneath or within the liquid. Liquid particles are ejected from the surface of the liquid into the surrounding air following the disintegration of capillary waves produced by the ultrasound. This technique can produce a very fine dense fog or mist. Aerosol mists produced by ultrasound are preferred because a smaller particle size of the aerosol can be obtained with the ultrasonic waves. One of the major shortcomings of inhalers and nebulizers is that there are no directed aerosol to the target without an air stream, which decreases the efficiency of ultrasound.

Contact physiotherapy applies ultrasonic waves directly to tissue in an attempt to produce a physical change in the tissue. In conventional ultrasound physiotherapy, an ultrasonic transducer contacts the tissue via a coupling medium. Ultrasonic waves produced by the transducer travel through the coupling medium and into the tissue. The coupling medium is typically a bath of liquid, a jelly applied to the surface to be treated, or a water-filled balloon. Conventional techniques provide ultrasonic waves having an intensity of from about 0.25 w/cm$^2$ to 3 w/cm$^2$ at a frequency of from about 0.8 to 3 Megahertz. The treatment is applied to a skin surface for from about 1 to 30 minutes, two or three times a week. The coupling medium can provide a cooling effect which dissipates some of the heat energy produced by the ultrasonic transducer. More importantly, a coupling medium or direct contact between the tissue and the ultrasonic transducer is necessary to transmit the ultrasonic waves from the transducer to the skin surface because ambient air is a relatively poor medium for the propagation of ultrasonic waves.

Several beneficial effects have been reported from contact ultrasound physiotherapy. For example, the following effects have been associated with contact ultrasound physiotherapy: local improvement of the blood circulation, heating of the tissue, accelerated enzyme activity, muscle relaxation, pain reduction, and enhancement of natural healing processes. Despite these beneficial effects, current techniques of medical physiotherapy using ultrasonic waves are limited by the necessity of providing a direct contact interface between the ultrasonic transducer and the tissue to maintain an effective transmission of the ultrasonic waves from the transducer to the tissue. The necessity of direct contact with or without a coupling medium makes current methods undesirable. Some tissue conditions may be accessible to contact ultrasound devices but would be impractical for contact ultrasound treatment. For example, fresh or open wounds resulting from trauma, burns, surgical interventions are not suitable for direct contact ultrasound treatment because of the structural of the structural nature of the open wound and the painful condition associated with those wounds. Moreover, conventional contact ultrasound may have a destructive effect on these types of open wounds due to the close proximity of an oscillating tip of an ultrasonic transducer relative to the already damaged tissue surface.

OBJECT OF THE INVENTION

It is an object of the invention to provide a method and device for treating wounds.

It is also an object of this invention to provide a method and device for treating wounds using ultrasonic waves.

It is another object of the invention to provide a method and device for delivering drugs and irrigation to wounds.

It is a yet another object of the invention to provide a method and device for the mechanical cleansing and debridement of wounds.

It is a further object of the invention to provide a method and device for increasing blood flow in a wound area.

It is a yet further object of the invention to treat a wound by spraying the surface of the wound with an aerosol mist produced by ultrasonic waves.

These and other objects of the invention will become more apparent from the discussion below.

SUMMARY OF THE INVENTION

The present invention concerns a method and device for spraying a wound surface to deliver drugs, kill bacteria, or cleanse a surface by non-contact application of ultrasonic waves. The ultrasonic waves are applied to the wound without requiring direct or indirect (via a traditional coupling medium) contact between an ultrasonic wave transducer and the wound to be sprayed.

Ultrasonic sprayers (Sonic and Materials Inc., Misonix Inc., Sono-Tek Inc.; U.S. Pat. Nos. 4,153,201, 4,655,393, and 5,516,043) typically operate by passing liquid through the central orifice of the tip of an ultrasound instrument. Known applications are essentially industrial, such as a burner or device for coating of surfaces. No ultrasound wound or biological tissue treatment application with such a device has been indicated, with the exception of ultrasound liposuction.

According to the present invention a directed spray of liquid particles produced by contact of the liquid with a free end surface of an ultrasonic transducer is directed onto a wound. The ultrasonic waves cause the spray to project outwardly from the distal end surface, and the particles of the spray provide a medium for propagation of the ultrasonic waves emanating from the distal end surface.

Figure 8:
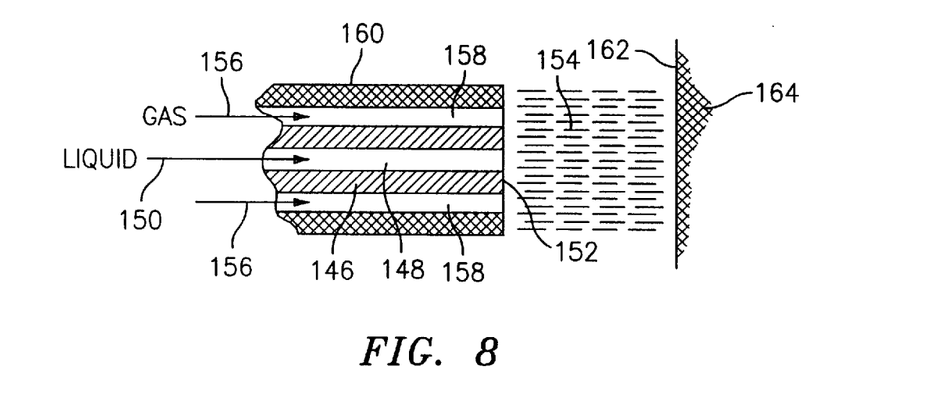

In the method of the present invention, particle spray created by low frequency ultrasound waves and directed at the surface of a wound, can deliver drugs, kill bacteria on the wound, increase blood flow, and/or remove dirt and other contaminants from that surface (mechanical cleansing). This method of drug delivery is particularly advantageous on tissues for which local topical application of a drug is desirable yet contact with the tissue is to be avoided. Furthermore, the low frequency ultrasound waves used in the method energize the drug and cause penetration of the drug below the surface of the tissue. Finally, the bacteria killing method is effective when applied to the surface whether the liquid sprayed is a drug (an antiseptic or antibiotic), oil, saline, distilled water, or the like.

In a device according to the invention, a spray is produced by first delivering liquid to the free distal end surface of an ultrasound tip through the axial (center) orifice or hose. After liquid is delivered to the free distal end surface, ultrasonic waves create the spray, which is directed to a particular targeted surface such a wound. Simultaneously ultrasonic waves are delivered to the wound surface through the spray.

The device must have a nozzle made from a rigid material such as steel (non-disposable) or plastic (disposable). The nozzle allows liquid to be delivered to a lateral surface of the transducer tip or directly to the distal side (radiation surface) of the ultrasound instrument to be sprayed.

BRIEF DESCRIPTION OF THE DRAWINGS:

FIG. 1 is a perspective view of an ultrasonic wound treatment system for use according to the invention;

FIG. 2 is a partial cross-sectional view of the distal portion of an ultrasonic wound treatment device of the invention with a central orifice;

FIG. 3 is a partial cross-sectional view of the distal portion of an ultrasonic wound treatment device of the invention with no central orifice;

FIG. 4 is a partial cross-sectional view of the distal portion of an ultrasonic wound treatment device of the invention with focused ultrasound;

FIG. 5 is a partial cross-sectional view of the distal portion of an ultrasonic wound treatment device of the invention with a thread on a radial surface;

FIG. 6 is a partial cross-sectional view of the distal portion of an ultrasonic wound treatment device of the invention with a thread in a central orifice;

FIG. 7 is a partial cross-sectional view of the distal portion of a device for spraying where fluid is delivered to a lateral or radiation surface of the transducer tip by tube or sleeve and gas is delivered through the ultrasound tip's central orifice;

FIG. 8 is a partial cross-sectional view of the distal portion of a device for spraying where gas is delivered to a lateral or radiation surface of the transducer tip the through housing or bushing by perimeter of the tip and liquid is delivered through the ultrasound tip's central orifice;

FIG. 9 is a view illustrating use of a bushing for better effect of ultrasound standing waves to treat wounds; and FIG. 10 is a partial cross-sectional view of a nozzle for ultrasound wound treatment using two tubes, one for carrying gas such a oxygen and another for carrying liquid such as a therapeutic agent.

DETAILED DESCRIPTION OF THE INVENTION

The present invention is a method and device, which uses ultrasonic wave energy to treat wounds. The device comprises a generator of electrical signals and a handpiece having an ultrasound transducer tip. The handpiece also comprises a tube for delivering drug to the radiation surface of the ultrasound tip.

The invention can perhaps be better appreciated from the drawings. In FIG. 1, a system 10 according to the invention comprises an ultrasound generator 12 in operative connection through cable 14 with an ultrasound handpiece 16. Handpiece 16 comprises an ultrasound nozzle 18 and a transducer 20 and is in fluid communication through connecting member 22 with liquid reservoir 24. Liquid dispensed from reservoir 24 contacts the distal end or radiation surface 26 of nozzle 18, resulting in a spray 30 that is directed toward the surface 32 of wound 34. In this fashion liquid is sprayed on the wound surface while ultrasonic waves are delivered to the wound.

FIG. 2 is a schematic representation of a cross-section of an ultrasonic nozzle tip 36 for wound treatment with a central lumen or orifice 38, as used in a device of the present invention. Liquid from a reservoir (not shown) is delivered in the direction of arrow 40 to the distal end 42 of ultrasound tip 36 through central orifice 38 to create ultrasound mist 44, which is directed to the surface 46 of a wound 48.

FIG. 3 is a schematic representation of a cross-section of an ultrasonic nozzle tip 50 for wound treatment with no central orifice, as used in a device of the present invention. Liquid from a reservoir (not shown) is delivered in the direction of arrow 52 to a solid distal end 54 of ultrasound tip 50 through a lumen 55 in tubing 56, to create ultrasound mist 58. Ultrasound mist 58 is directed to the surface 60 of a wound 62.

FIG. 4 is a schematic representation of a cross-section of an ultrasonic nozzle tip 66 with focused energy for wound treatment with no central orifice, as used according to the invention. Liquid 68 from a reservoir (not shown) is delivered in the direction of arrow 68 to the solid distal end 70 of ultrasound tip 66 through a lumen 71 in tubing 72 to create an ultrasound mist 74 that is directed to a focal point 76 on the surface 78 of a wound 80. Ultrasound tip distal end 70 is curved, e.g., elliptical, oval, etc.

FIG. 5 is a schematic representation of a cross-section of an ultrasonic nozzle tip 84 for wound treatment with grooves 86 on a radial surface 88. Liquid from a reservoir (not shown) is delivered in the direction of arrow 90 to radial surface 88 through a lumen 91 in tubing 92, to create an ultrasound mist 94. Ultrasound mist 94 is directed to the surface 96 of a wound 98. Grooves 86 can alternatively be threads or rings.

FIG. 6 is a schematic representation of a cross-section of an ultrasonic nozzle tip 102 for wound treatment with thread 104 in a central lumen or orifice 106. Liquid from a reservoir (not shown) is delivered in the direction of arrow 108 through central orifice 106 to the distal end 110 of ultrasound tip 102 to create an ultrasound mist 112. Ultrasound mist 112 is directed to the surface 114 of a wound 116.

FIG. 7 is a schematic representation of a cross-section of an ultrasonic nozzle tip 120 for wound treatment with a central lumen or orifice 122. Liquid from a reservoir (not shown) is delivered in the direction of arrow 124 through a lumen 128 in tubing 130 to the distal end 132 of ultrasound tip 120 to create an ultrasound mist 134. A gas such as oxygen is delivered in the direction of arrow 136 through central orifice 122. Ultrasound mist 134 is directed to the surface 138 of wound 140. Alternatively, liquid can be delivered in the direction of arrow 136 through central orifice 122 and gas can be delivered in the direction of arrow 124 through lumen 128.

FIG. 8 is a schematic representation of a cross-section of an ultrasonic nozzle tip 146 for wound treatment with a central lumen or orifice 148. Liquid from a reservoir (not shown) is delivered to the distal end 152 of ultrasound tip 146 through central orifice 148, to create an ultrasound mist 154. Ultrasound mist 154 also carries a gas such as oxygen, delivered in the direction of arrow 156 through annular channel 158 formed by bushing 160. Ultrasound mist 154 contacts the surface 162 of wound 166. Alternatively, gas liquid can be delivered in the direction of arrow 156 through annular channel 158 and gas can be delivered in the direction of arrow 150 through central orifice 148.

Figure 9:
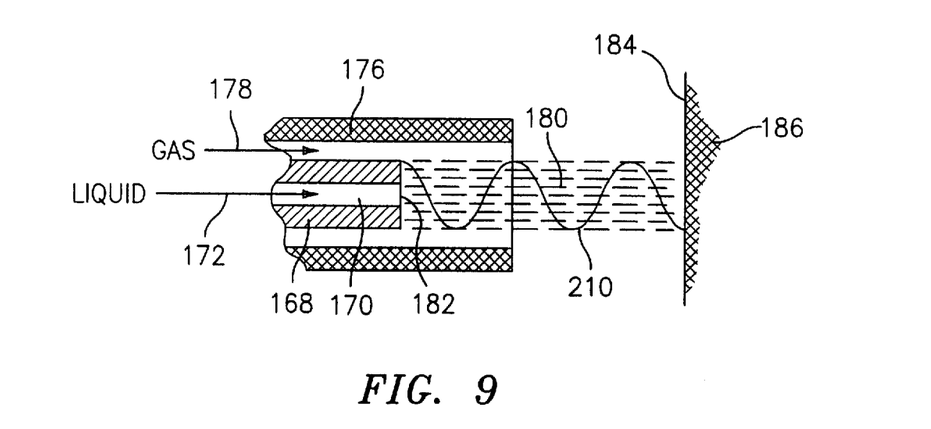

FIG. 9 is a schematic representation of a cross-section of an ultrasonic nozzle tip 168 for wound treatment with a central lumen or orifice 170 and an expanded bushing 176, which creates better conditions for standing waves. Liquid from a reservoir (not shown) is delivered in the direction of arrow 172. Substantially annular channel 174 is formed by expended bushing 176, and gas such as oxygen is delivered through annular channel 174 in the direction of arrow 178. An ultrasound mist 180 created at the distal end 182 of ultrasound tip 168 is directed at the surface 184 of wound 186. Alternatively, liquid can be delivered in the direction of arrow 178 through annular channel 174 and gas can be delivered in the direction of arrow 172 through central orifice 170.

Figure 10:
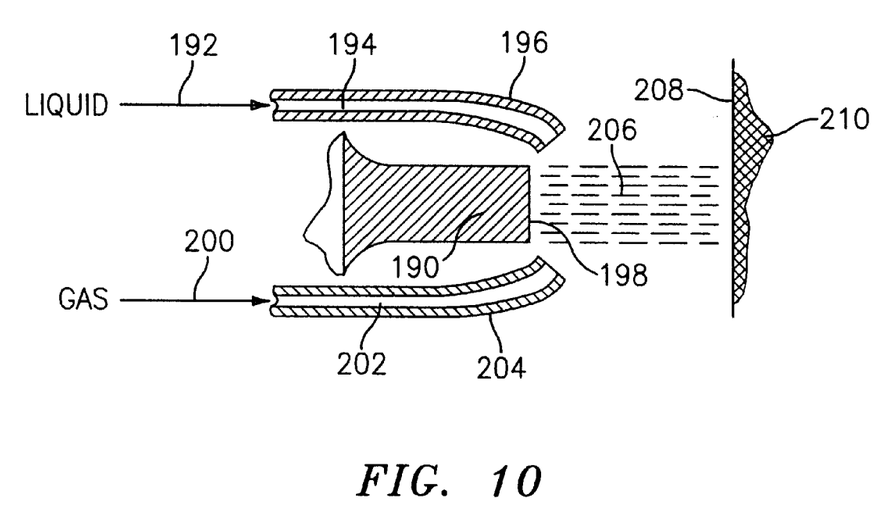

Fig. 10 is a schematic representation of an ultrasonic nozzle tip 190 with no central orifice, where liquid is delivered from a reservoir (not shown) in the direction of arrow 192 through a lumen 194 in tubing 196 to the distal end 198 of tip 190. A gas such as oxygen is delivered from a gas source (not shown) in the direction of arrow 200 through a lumen 202 in tubing 204 to tip distal end 198. An ultrasound mist 206 created at tip distal end 198 is directed to the surface 208 of wound 210.

Figure 1:
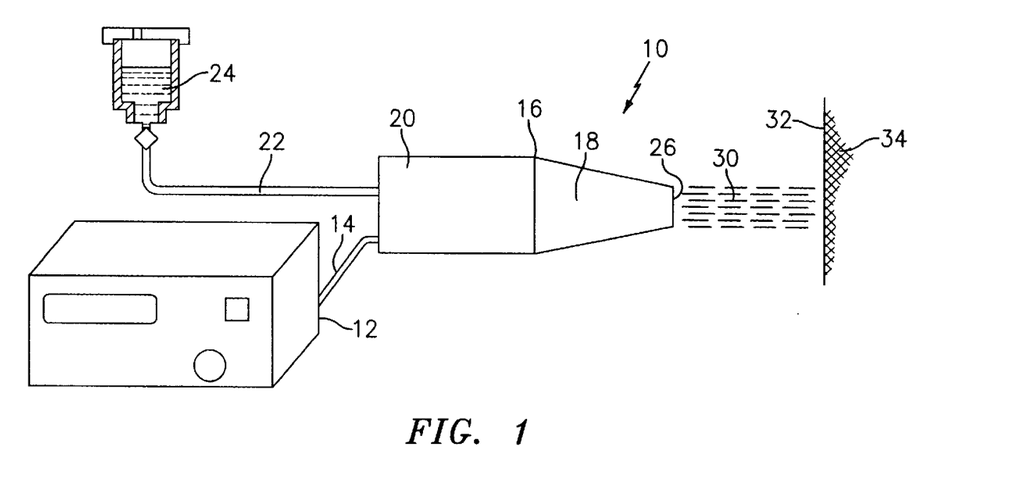
Figure 2:
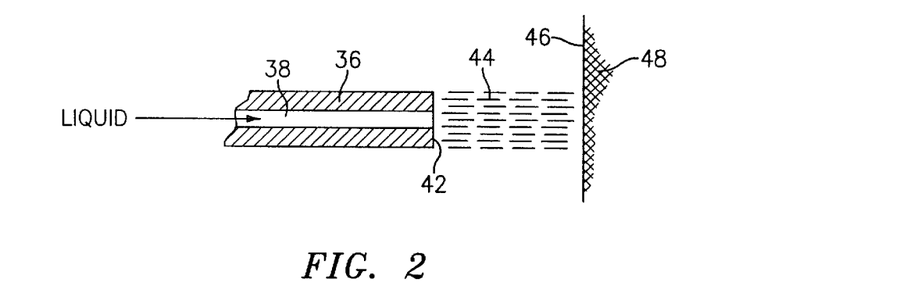
Figure 3:
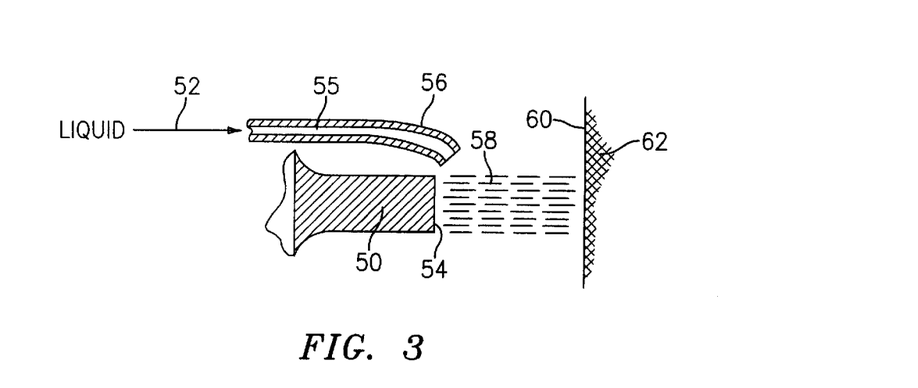
Figure 4:
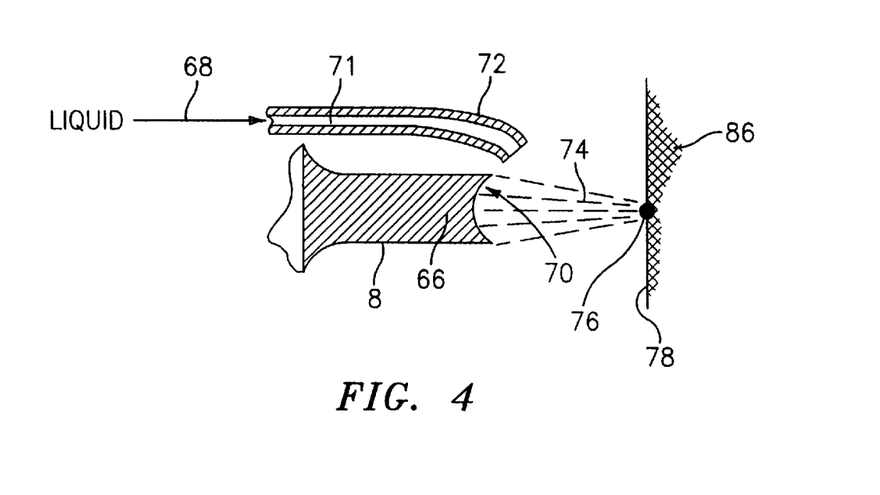

The cross-section of the ultrasonic nozzle tip can be circular, oval, elliptical, rectangular, multi-angular, trapezoidal, or a combination thereof. The distal end shape of the ultrasound nozzle tip may be the same or different, such as rectangular, elliptical, oval, spherical, conical, curved, stepped, with chamfer, etc. The most preferred shape is rectangular, due to radiation beams from the ultrasonic nozzle tip surface being fully directed to the target (wound). With the spherical, elliptical and oval shaped ends, radiation beams are focussed at a focal point, as shown, for example, in FIG. 4. With distal ends of other shapes, some of the radiation beams spread before reaching the target.

Figure 5:
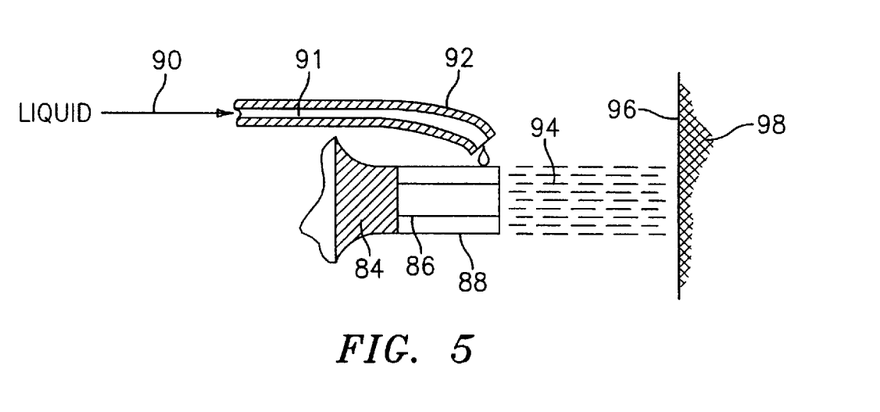
Figure 6:
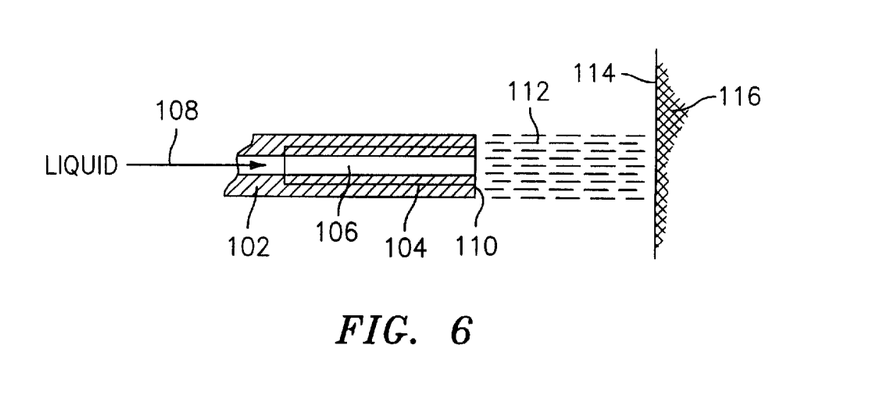

Radial side surface(FIG. 5) of distal end and central orifice (FIG. 6) of the ultrasond tip may have slot (groove)or thread for liquid to be directed to the radiation surface, which increases the liquid pressure.

Figure 7:
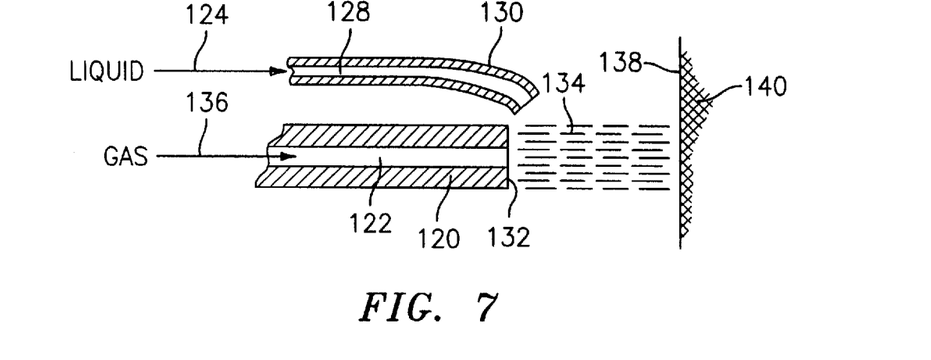

Since local tissue oxygenation can stimulate tissue regeneration and prevent infection in wound treatment, the method of the present invention includes the mixing and delivery of oxygen and sprayed liquid (saline, water, therapeutic agent, etc.) as shown, for example, in FIG. 7. In this case the liquid spray delivers oxygen or another gas to the wound. Gas or liquid can be delivered via tubing (FIG. 7) or housing (FIG. 8).

The step of producing the spray can further include operating the transducer to produce ultrasonic waves having a frequency of from about 18 to 10000 kHz. Although a frequency of 1 to 18 kHz can be used, this range should be avoided since this range of sound wave is uncomfortable to the patient and operator. The preferred range of frequency is from about 30 to 100 kilohertz, the most preferred frequency being about 40 kHz.

The distance of separation between the distal free end surface of the transducer and the surface to be sprayed is preferably from about 0.1 to 20 inches.

One of the benefits of the present invention is the use of the ultrasound standing waves for wound treatment. Ultrasound standing waves 210 occur when an ultrasound nozzle tip is activated through the air toward the wound surface as a result of incident and reflected waves from the wound surface, which creates ultrasonic radiation pressure. Standing waves 210, actually ultrasound radiation pressure, occur when the distance between the distal end of the transducer nozzle tip (as a radiant of ultrasound waves) and the reflected surface (wound surface) is: n . $\lambda/2$ ($\lambda$=wave length, n=integer). To reach this preferred distance and therefore this effect in wound treatment practice, the ultrasound transducer or tip must be moved back and forth toward the wound by the operator.

The standing waves are more effective in limited space or area as a tube. In this case use of a bushing 176 (FIG. 9) increases ultrasound radiation pressure. The bushing may or may not be disposable part on the distal end.

The liquid can further include any drug (antibiotic, anticeptic, etc.), saline, water (distilled or regular), or oil for application to the tissue.

In addition, the method of the invention can include directing the spray onto the surface for from about I second to about 30 minutes, dependant upon the condition and size of the wound. This can be done on a daily or semi daily basis, or two-three times per week or month.

The method of the present invention permits application of ultrasonic waves to the wound without establishing contact, directly or indirectly, between the ultrasonic transducer and the wound. For example, surfaces of the human body especially suited for treatment with the method of the present invention include infected and/or inflamed situations in open wounds, including trauma or gun shut wounds, and fire and chemical burns.

In addition, the method of the present invention is particularly suited to directing a spray into orifices or other body crevices that are difficult to access.

This method of wound treatment has a several advantages. First, this method topically applies medicines such as liquid antibiotics to the wound surface without the need to contact an infected, inflamed or painful tissue with an instrument. Second, a significant debridement, cleansing and bactericidal effect can occur, when spraying a wound surface using the method of the present invention. And third, aside from the bactericidal effect and advantages of non-contact treatment, use of the method of the present invention permits a significant reduction in volume used of liquid medicine used as compared with traditional methods for wound treatment. Similarly, this allows for precise dosage of the sprayed liquid to permit a user, such as a physician to administer the desired volume of liquid at a desired rate and duration.

The method of the present invention decreases healing times for inflammatory and purulent infected wounds, up to 1.5 to 2 times faster than traditional methods. This effect results from a bactericidal, blood flow increasing and mechanical cleansing effect of the atomized spray particles, which have ultrasound energy due to the ultrasonic waves.

The ultrasonic spray mechanically scrubs the surface of tissue to remove dirt, dead tissue, and purulent buildup on the tissue surface.

The mentioned healing effect also results of energized and highly activated antibiotics, drug penetration into the tissue surface up to 0.5 mm in depth under influence of ultrasound waves. Additionally, a combination of the low frequency ultrasonic waves and the sonicated medicines (highly activated by ultrasonic energy) destroy the surface bacteria to result in a higher disinfecting property of sonicated liquids as compared to ordinarily applied liquids. The spray of the present method also stimulates healthy cell growth to aid in granulization and epithelization of the healing tissue. Other applications of the method can be directed to non-medical uses such as cleansing, sterilizing and coating surfaces of objects and food. The method of the present invention offers an approach that may re-establish use of some traditional antibiotics and establish a method fighting bacteria without antibiotics when necessary.

The effect of the method of the present invention in highly activating antibiotics may allow some traditional antibiotics to overcome bacteria which have become resistant to that antibiotic. Moreover, independent of the sonication effect of the antibiotics, the low frequency ultrasonic waves applied in the method of the present invention physically destroy bacteria. The combination of the highly activated antibiotics and of the low frequency ultrasonic waves in the method of the present invention produce a strong bactericidal effect not found in mere topically application or orally ingested antibiotics. This combined effect has been shown to significantly increase the healing of purulent infected wounds.

The present method also provides a system of non-contact drug delivery without using a compression sprayer system. This simplifies the design of a non-contact drug delivery sprayer and reduces the weight of the sprayer. More importantly, not using compression to propel the atomized particles preserves the ultrasound energy carried by the spray particles.

It is provided that the driving frequency of the transducer is held constant, modulated or pulsed during treatment and that the distal radiation surface is driven with a sinusoidal, rectangular, trapezoidal or triangular wave form.

The method of the present invention provides a method of compressionless non-contact drug delivery.

It is to be understood, however, that other expedients known to those skilled in the art or disclosed herein, may be employed without departing from the spirit of the invention or the scope of the appended claims.

What is claimed is:

1. A method for treating a wound comprising the steps of:

providing a transducer having a distal radiation surface arranged a distance from the surface of the wound for emitting ultrasonic energy and defining an orifice therethrough, an inner surface of the orifice includes at least one of a groove and a ring;

introducing a fluid to the distal radiation surface via the orifice to produce a spray; and delivering the emitted ultrasonic energy to the wound through the spray, wherein the ultrasonic energy penetrates the wound tissue to a beneficial depth to provide a bactericidal and a therapeutic effect for decreasing the healing time for the wound.

2. The method according to claim 1, wherein the transducer operates at a frequency from 18 kHz to 10,000 MHz.

3. The method according to claim 1, wherein the transducer operates at a frequency from 35 kHz to 45 kHz.

4. The method according to claim 1, wherein the distal radiation surface is positioned from 0.1 to 20 inches from the surface of the wound.

5. The method according to claim 1, wherein the fluid includes one or more components selected from the group consisting of gas, antibiotics, antiseptics, saline solutions, oils, and water.

6. The method according to claim 1, wherein the delivering step includes the step of delivering the emitted ultrasonic energy for a predetermined time for achieving the bactericidal and therapeutic effects, and further comprising the step of repeating the treatment method until the wound is healed.

7. The method according to claim 1, wherein the transducer is driven by at least one of a constant, pulsed, and modulated frequency, and wherein the driving wave form of the transducer is selected from the group consisting of sinusoidal, rectangular, trapezoidal and triangular wave forms.

8. The method according to claim 1, wherein the therapeutic effect is selected from the group consisting of increasing blood flow to the wound, mechanically cleansing the wound, stimulating cell growth, providing at least one medicament to the wound, and penetrating at least one medicament through the surface of the wound.

9. The method according to claim 1, further comprising the step of providing at least one more orifice through the transducer, and further comprising the step of introducing another fluid to the distal radiation surface via one orifice of the at least one more orifice.

10. The method according to claim 9, further comprising the step of facilitating the creation of ultrasonic standing waves by providing a different length for the at least one more orifice than the length of the orifice.

11. The method according to claim 1, further comprising the step of introducing a second fluid to the distal radiation surface, and wherein the step of delivering the emitted ultrasonic energy to the wound includes the step of delivering the second fluid to the wound.

12. The method according to claim 1, wherein the distal radiation surface has a shape selected from the group consisting of rectangular, elliptical, oval, spherical, conical, curved, stepped, and with chamfer.

13. An apparatus for treating a wound comprising:

a transducer having a distal radiation surface arranged a distance from the surface of the wound for emitting ultrasonic energy and defining an orifice therethrough, an inner surface of the orifice includes at least one of a groove and a ring; and means for introducing a fluid to the distal radiation surface via the orifice to produce a spray, wherein the generated ultrasonic energy is delivered to the wound through the spray, and wherein the ultrasonic energy penetrates the wound tissue to a beneficial depth to provide a bactericidal and a therapeutic effect for decreasing the healing time for the wound.

14. The apparatus according to claim 13, wherein the transducer operates at a frequency from 18 kHz to 10,000 MHz.

15. The apparatus according to claim 13, wherein the transducer operates at a frequency from 35 kHz to 45 kHz.

16. The apparatus according to claim 13, wherein the distal radiation surface is positioned from 0.1 to 20 inches from the surface of the wound.

17. The apparatus according to claim 13, wherein the fluid includes one or more components selected from the group consisting of gas, antibiotics, antiseptics, saline solutions, oils, and water.

18. The apparatus according to claim 13, wherein the therapeutic effect is selected from the group consisting of increasing blood flow to the wound, mechanically cleansing the wound, stimulating cell growth, providing at least one medicament to the wound, and penetrating at least one medicament through the surface of the wound.

19. The apparatus according to claim 13, wherein the transducer includes at least one more orifice, and further comprising means for introducing another fluid to the distal radiation surface via one orifice of the at least one more orifice.

20. The apparatus according to claim 13, wherein the distal radiation surface has a shape selected from the group consisting of rectangular, elliptical, oval, spherical, conical, curved, stepped, and with chamfer.

21. A method for treating a wound comprising the steps of:

generating ultrasonic energy at a distance from the surface of the wound, such that the generated ultrasonic energy propagates through a gaseous medium;

introducing a fluid in at least one propagation path of the generated ultrasonic energy to produce a spray, wherein the fluid is introduced via an orifice aligned with the at least one propagation path, the orifice includes an inner surface having at least one of a groove and a ring; and delivering the generated ultrasonic energy to the wound through the spray, wherein the ultrasonic energy penetrates the wound tissue to a beneficial depth to provide a bactericidal and a therapeutic effect for decreasing the healing time for the wound.

22. The method according to claim 21, further comprising the step of introducing a second fluid in the at least one propagation path, and wherein the step of delivering the generated ultrasonic energy to the wound includes the step of delivering the second fluid to the wound.

* * * * *